United States Patent
Nicholson

(10) Patent No.: US 7,105,480 B1
(45) Date of Patent: Sep. 12, 2006

(54) METHOD OF TREATMENT AND AGENTS USEFUL FOR SAME

(75) Inventor: Geoffrey Charles Nicholson, Victoria (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 09/632,074

(22) Filed: Aug. 2, 2000

(30) Foreign Application Priority Data

Aug. 3, 1999 (AU) .................................... PQ1999

(51) Int. Cl.
*A61K 38/17* (2006.01)
*A61K 38/18* (2006.01)
*C07K 14/47* (2006.01)
*C07K 14/51* (2006.01)

(52) U.S. Cl. .......................... 514/2; 514/12; 530/350; 530/399; 530/402

(58) Field of Classification Search .................... 514/2, 514/12; 530/399
See application file for complete search history.

(56) References Cited

U.S. PATENT DOCUMENTS 6,352,970 B1 * 3/2002 Ke et al. ........................ 514/2

OTHER PUBLICATIONS

Liu et al. American Society for Bone and Mineral Research, 19th Annual Meeting, Sep. 10-14, 1997, Cincinati, Ohio.*
Auwerx et al. "Leptin" *Lancet* 1998; 351: 737-742.
Bonner & Laskey, "A Film Detection Method for Tritium Labelled Proteins and Nucleic Acids in Polyacrylamide Gels" *Eur. J. Biochem.* 1974; 46: 83-88.
Friedman et al., "Leptin and the regulation of body weight in mammals" *Nature* 1998; 395: 763-770.
Marmur & Doty, "Determination of the Base Composition of Deoxyribonucleic Acid from its Thermal Denaturation Temperature" *J. Mol. Biol.* 1962; 5: 109-118.
Matsuzaki et al., "Osteoclast Differentiation Factore (ODF) Induces Osteoclast-like Cell Formation in Human Peripheral Blood Mononuclear Cell Cultures", *Biochem. Biophys. Res. Commun.* 1998; 246: 199-204.
Quinn et al., "A Combination of Osteoclast Differentiation Factor and Macrophage-Colony Stimulating Factor is Sufficient for both Human and Mouse Osteoclast Formation in Vitro", *Endocrinology* 1998; 139: 4424-4427.
Simonet et al., "Osteoprotegerin: A Novel Secreted Protein Involved in the Regulation of Bone Density", *Cell* 1997; 89: 309-319.
Suda et al. "Modulation of Osteoclast Differentiation" *Endocrine Reviews* 1992; 13: 66-80.
Suda et al. "Modulation of Osteoclast Differentiation and Function by the New Members of the Tumor Necrosis Factor Receptor and Ligand Families" *Endocrine Reviews* 1999; 20: 345-357.
Yasuda et al. "Identity of Osteoclastogenesis Inhibitory Factor (OCIF) and Osteoprotegerin (OPG): A Mechanismm by which OPG/OCIF Inhibits Osteoclastogenesis *in Vitro*" *Endocrinology* 1998; 139: 1329-1337.

* cited by examiner

*Primary Examiner*—Christine J. Saoud
(74) *Attorney, Agent, or Firm*—Knobbe, Martens, Olson & Bear, LLP

(57) ABSTRACT

The present invention relates generally to a method of modulating bone resorption and to agents useful for same. More particularly, the present invention provides for the use of leptin and its derivatives, homologues, analogues, antagonists or agonists to modulate osteoclastogenesis. Even more particularly, the present invention contemplates the treatment of disorders characterised by or associated with excessive bone resorption such as but not limited to osteoporosis and Paget's disease. The present invention further provides for the use of leptin and its derivatives, homologues, analogues, antagonists and agonists in the manufacture of a medicament for the modulation of bone resorption.

9 Claims, 6 Drawing Sheets

A

B

C

METHOD OF TREATMENT AND AGENTS USEFUL FOR SAME

This Application claims priority under 35 U.S.C. §119(a) of Australian Provisional Patent application No. PQ1999, filed Aug. 3, 1999.

FIELD OF THE INVENTION

The present invention relates generally to a method of modulating bone resorption and to agents useful for same. More particularly, the present invention provides for the use of leptin and its derivatives, homologues, analogues, antagonists or agonists to modulate osteoclastogenesis. Even more particularly, the present invention contemplates the treatment of disorders characterised by or associated with excessive bone resorption such as but not limited to osteoporosis and Paget's disease. The present invention further provides for the use of leptin and its derivatives, homologues, analogues, antagonists and agonists in the manufacture of a medicament for the modulation of bone resorption.

BACKGROUND OF THE INVENTION

Bibliographic details of the publications referred to by author in this specification are collected at the end of the description. Nucleotide and amino acid sequences are referred to by a sequence identifier, i.e. (SEQ ID NO: 1), (SEQ ID NO:2), etc. A sequence listing is provided after the claims.

Reference to any prior art in this specification is not, and should not be taken as, an acknowledgment or any form of suggestion that this prior art forms part of the common general knowledge in Australia or any other country.

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

The regulation of bone metabolism is a multifaceted process requiring the tight control of bone resorption and bone formation. The latter is the primary function of osteoblasts whereas bone resorption involves osteoclasts.

Osteoclasts are multinucleate cells formed in bone marrow by the fusion of cells from the monocyte/macrophage lineage (Suda et al., 1992; Quinn et al., 1998). A variety of factors play a role in regulating osteoclast formation including growth factors, systemic hormones and cell contact with marrow stroma.

A number of proteins have been identified which are involved in the process of osteoclastogenesis. Osteoprotegerin, also known as osteoclastogenesis inhibitory factor (OPG and OCIF, respectively), is a secreted member of the TNF receptor superfamily that blocks osteoclast differentiation both in vitro and in vivo (Yasuda, et al., 1998; Simonet et al., 1997). The cloning of a membrane bound ligand for OPG (OPG-ligand [OPGL]) resulted in the identification of an essential signal for proliferation and fusion of osteoclast progenitors (Yasuda, et al., 1998). This protein, also called osteoclast differentiation factor (ODF), is expressed on the plasma membrane of osteoblasts/marrow stromal cells and has a membrane bound receptor (in contrast to the soluble receptor, OPG/OCIF) identified as receptor activator of NF-kappa β (RANK). OPGL/ODF has also been termed TNF-related activation-induced cytokine (TRANCE) and RANK-ligand (RANKL). The combination of M-CSF and a soluble form of recombinant ODF, lacking the transmembrane domain, is necessary and sufficient to stimulate osteoclast generation, in the absence of osteoblast or stromal cells, from either murine spleen cells or human monocytes (Matsuzaki et al., 1998; Quinn et al., 1988).

Leptin, a cytokine produced primarily by mature adipocytes, is linked to food intake and energy expenditure (Friedman and Halaas, 1998) but also has activity in neuroendocrine, metabolic, reproductive and haemopoetic pathways (Auwerz and Staels, 1998).

In work leading up to the present invention, the inventors investigated the role of leptin in the bone microenvironment. The inventors have now identified leptin as a regulator of osteoclastogenesis. This provides the basis for the development of a range of medicaments for modulating bone resorption.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention contemplates a method of modulating bone resorption in a human or animal, said method comprising administering to said human or animal an effective amount of leptin or a derivative, homologue, analogue, chemical equivalent, antagonist or agonist thereof for a time and under conditions sufficient for the modulation of osteoclastogenesis.

Another aspect of the present invention provides a method for inhibiting, reducing or otherwise delaying onset or progression of bone resorption in a human or animal, said method comprising administering to said human or animal an effective amount of a leptin as hereinbefore defined for a time and under conditions sufficient to inhibit, reduce or otherwise delay onset or progression of osteoclastogenesis.

Yet another aspect of the present invention is directed to the use of leptin as hereinbefore defined in the manufacture of a medicament in the treatment of a disease condition involving excess bone resorption.

Still yet another aspect of the present invention provides a composition useful in the modulation of bone resorption comprising leptin as hereinbefore defined and one or more pharmaceutically acceptable carriers and/or diluents.

Figure 1:
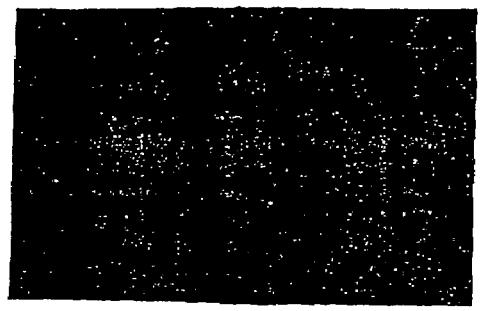
FIG. 1 is a photographic representation showing generation of TRAP+ve multinuclear cells (MNC) and monoclear (Mono) cells. A colour version of this figure is available by request from the Applicant.
Figure 1:
Figure 1:
Figure 1:
Figure 1:
Figure 1:

Abbreviations used in the subject specification are defined in Table 1.

TABLE 1

ABBREVIATIONS

| | |
|---|---|
| TNF | Tumour necrosis factor |
| OPG (OCIF) | Osteoprotegerin; Osteoclastogenesis Inhibitory Factor Membrane bound ligand for OPG; osteoclast |
| OPGL (ODF) | differentiation factor (same as TRANCE, TNF-related activation-induced cytokine) |
| RANKL | Ligand for RANK (same as OPGL/ODF/TRANCE) |
| RANK | Receptor activator of NP-kappa β |
| M-CSF | Macrophage-colony stimulating factor |
| Mono | Mononuclear cell |
| MNC | Multinuclear cell |
| TRAP | Tartrate-resistant acid phosphatase |
| PBMC | Peripheral blood mononuclear cell |
| PBS | Phosphate buffered saline |
| FCS | Fetal calf serum |
| TGFβ | Transforming growth factor - β |
| RT-PCR | Reverse transcriptase polymerase chain reaction |
| CTR | Calcitonin receptor |

DETAILED DESCRIPTION OF THE PREFERRED EMBODIMENTS

The present invention is predicated in part on the identification of leptin as a potent inhibitor of oseoclastogenesis. This provides a means for modulating bone resorption.

Accordingly, one aspect of the present invention contemplates a method of modulating bone resorption in a human or animal, said method comprising administering to said human or animal an effective amount of leptin or a derivative, homologue, analogue, chemical equivalent, antagonist or agonist thereof for a time and under conditions sufficient for the modulation of osteoclastogenesis.

Reference herein to "leptin" includes reference to a polypeptide having the amino acid sequence set forth in (SEQ ID NO:2) or an amino acid sequence having at least 60% similarity thereto while retaining leptin activity or antagonist activity as well as a molecule encoded by the nucleotide sequence set forth in (SEQ ID NO:1) or a nucleotide sequence having at least about 60% similarity thereto or a nucleotide sequence capable of hybridising to (SEQ ID NO: 1) under low stringency conditions at 42° C.

Reference herein to a low stringency at 42° C. includes and encompasses from at least about 1% v/v to at least about 15% v/v formamide and from at least about 1 M to at least about 2 M salt for hybridization, and at least about 1 M to at least about 2 M salt for washing conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridisation, and at least about 0.01 M to at least about 0.15 M salt for washing conditions. In general, washing is carried out $T_m=69.3+0.41$ (G+C)% (Marmur and Doty, 1962). However, the $T_m$ of a duplex DNA decreases by 1° C. with every increase of 1% in the number of mismatch base pairs (Bonner and Laskey, 1974).

The term "leptin" is defined herein as including all derivatives, homologues, analogues, chemical equivalents, antagonists and agonists thereof.

The term "derivative" and its plural form includes parts, portions, fragments, regions, fusion molecules, mimotopes and mimetics.

Analogues and mimetics include molecules which contain non-naturally occurring amino acids as well as molecules which do not contain amino acids but nevertheless behave functionally the same as leptin. Natural product screening is one useful strategy for identifying analogues and mimetics. Natural product screening involves screening environments such as bacteria, plants, animals, rainforests, riverbeds, seabeds, aquatic environments, coral and antarctic or arctic environments for naturally occurring molecules which mimic, agonize or antagonize leptin of the present invention. Analogues of leptin contemplated herein include modifications to side chains, incorporation of unnatural amino acids and/or their derivatives during peptide synthesis and the use of crosslinkers and other methods which impose conformational constraints on the peptide molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code |
|---|---|
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |

TABLE 2-continued

| Non-conventional amino acid | Code |
|---|---|
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpencillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |

TABLE 2-continued

| Non-conventional amino acid | Code |
|---|---|
| N-benzylglycine | Nphe |
| N-(2-carbamylethyl)glycine | Ngln |
| N-(carbamylmethyl)glycine | Nasn |
| N(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Crosslinkers can be used, for example, to stabilize 3D conformations, using homo-bifunctional crosslinkers such as the bifunctional imido esters having $(CH_2)n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

All these types of modifications may be important to stabilize leptin. This may be important if leptin is used, for example, in the manufacture of a therapeutic composition.

The present invention further contemplates chemical equivalents of leptin. Chemical equivalents may not necessarily be derived from leptin itself but may share certain conformational or functional similarities. Alternatively, chemical equivalents may be specifically designed to mimic certain physiochemical properties of the polypeptides. Chemical equivalents may be chemically synthesized or may be detected following, for example, natural product screening.

The term "modulate" means that bone resorption may be stimulated, enhanced or otherwise increased or that it may be inhibited, retarded or otherwise reduced. Reduction in bone resorption is important for disease conditions involving an excess of bone resorption such as osteoporosis or Paget's disease. Preferably, the modulation involves a reduction in bone resorption.

Accordingly, another aspect of the present invention provides a method for inhibiting, reducing or otherwise delaying onset or progression of bone resorption in a human or animal, said method comprising administering to said human or animal an effective amount of a leptin as hereinbefore defined for a time and under conditions sufficient to inhibit, reduce or otherwise delay onset or progression of osteoclastogenesis.

Yet another aspect of the present invention is directed to the use of leptin as hereinbefore defined in the manufacture of a medicament in the treatment of a disease condition involving excess bone resorption.

Such conditions include osteoporosis and Paget's disease.

Accordingly, the present invention provides a composition useful in the modulation of bone resorption comprising leptin as hereinbefore defined and one or more pharmaceutically acceptable carriers and/or diluents.

Preferably, the composition inhibits, reduces or otherwise delays onset or progression of osteoclastogenesis.

The preferred form of a composition is as a pharmaceutical composition. Compositions suitable for injectable use include sterile aqueous solutions (where water soluble) and sterile powders for the extemporaneous preparation of sterile injectable solutions. They are generally stable under the conditions of manufacture and storage and must be preserved against the contaminating action of microorganisms such as bacteria and fungi. The carrier can be a solvent or dispersion medium containing, for example, water, ethanol, polyoil (for example, glycerol, propylene glycol and liquid polyethylene glycol, and the like), suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride.

Sterile injectable solutions are prepared by incorporating leptin as hereinbefore defined in the required amount in the appropriate solvent with various of the other ingredients enumerated above, as required, followed by, for example, filter sterilization by other appropriate means. In the case of sterile powders for the preparation of sterile injectable solutions, a preferred method of preparation includes vacuum drying and freeze-drying which yield a powder of the active ingredient plus any additional desired ingredient from a previously sterile-filtered solution.

When leptin is suitable protected, it may be orally administered, for example, with an inert diluent or with an assimilable edible carrier, or it may be enclosed in hard or soft shell gelatin capsule, or it may be compressed into tablets.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; and a lubricant such as magnesium stearate. Any material used in preparing any dosage unit form should be pharmaceutically pure and substantially non-toxic in the amount employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

Effective amounts of leptin will vary depending on the condition to be treated by may range from 0.001 ng/kg body weight to 100 mg/kg body weight. Leptin may be administered every minute or hourly, daily, weekly or monthly. Leptin may be used prophylactically or in the treatment of a disease condition.

The mode of administration may be intravenous, drip, infusion, oral, intraperitoneal, intra-bone, parenteral, inhalation, nasal drip, aerosol or rectal.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., USA.

The present invention further contemplates genetic modulation of endogenous leptin levels to thereby induce modulation of osteoclastogenesis.

Although not intending to limit the present invention to any one theory or mode of action, it is proposed herein that leptin inhibits osteoclastogenesis by antagonism of the osteoclastic effect of ODF by stimulation of OPG and inhibition of RANK expression.

The preferred subject for treatment is a human. The invention extends, however, to treatment in non-human animals such as primates, livestock animals (e.g. sheep, cows, pigs, goats, donkeys, horses), laboratory test animals (e.g. mice, rats, guinea pigs, hamsters), companion animals (e.g. dogs, cats) and captive wild animals.

EXAMPLE 1

Human Peripheral Blood Monocnuclear Cell (PBMC) Cultures

PBMC were isolated from the peripheral blood of haemochromatic patients and healthy volunteers. Whole blood was spun at 700 g and serum discarded. Blood cells were then diluted 1:1 in PBS and layered over ficoll at a volume ratio of 5:3 and spun at 400 g for 30 min. The top layer was discarded and the underlying layer containing the peripheral blood mononuclear cells (PBMCs) collected. PBMCs were washed in PBS to remove ficoll, collected via centrifugation (140 g) and resuspended in eagle's MEM/10% v/v FCS. PBMCs were seeded into 25 $cm^3$ tissue flasks (20–25×$10^6$ PBMCs/flask) and 4×4 mm cortical bovine bone slices (1×$10^6$ PBMCs/bone slice) and left to adhere for 2 hrs. Flasks and bone slices were rinsed to remove non-adherent cells and fresh media added.

EXAMPLE 2

Action of Leptin

The inventors proposed that systemic and/or bone marrow-derived leptin acted on osteoclast precursors (directly and/or indirectly) and regulated osteoclastogenesis. The inventors cultured adherent human peripheral blood monocytes (hPBMCs) on bone slices for 21 days in the presence of ODF and M-CSF (Quinn, 1998) with and without added leptin at various concentrations. The formation of multinuclear (MNC) osteoclasts was quantified by cytochemical staining for tartrate-resistant acid phosphatase (TRAP), $^{125}$I-salmon calcitonin ($^{125}$I-sCT) autoradiography for calcitonin receptor (CTR) and the identification of bone resorption lacunae by SEM.

Figure 2:
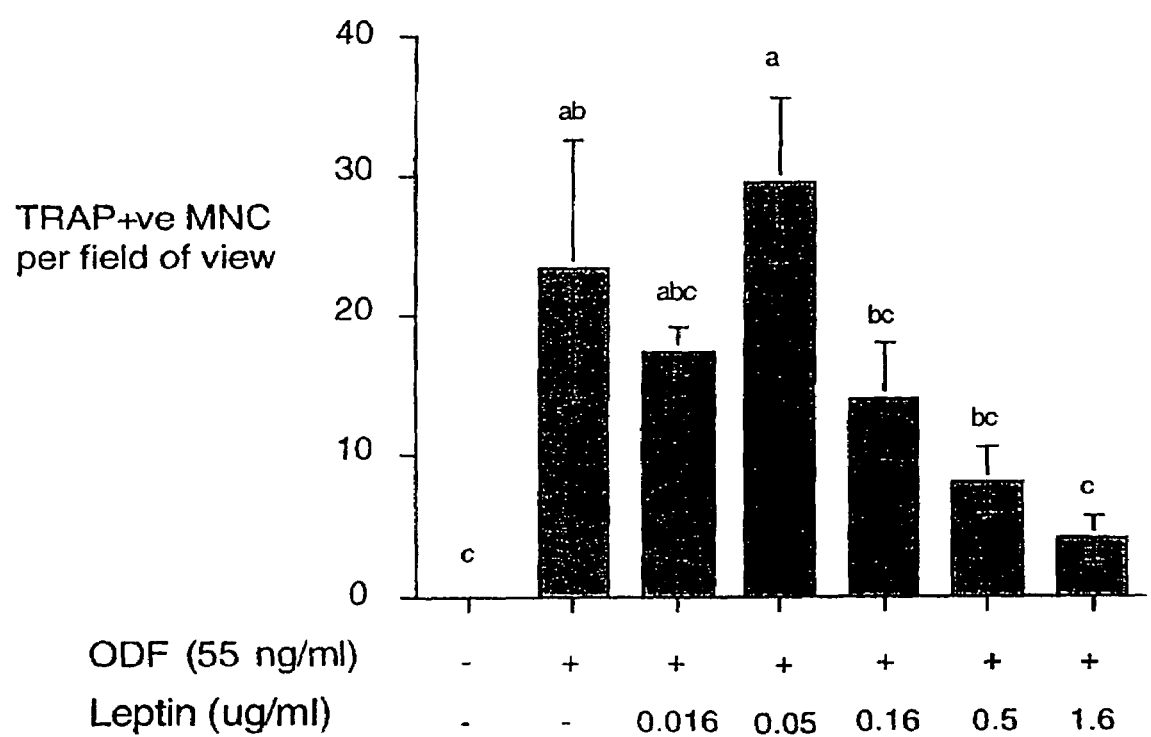
FIG. 2 is a graphical representation showing the effect of leptin on the generation of TRAP+ve multinuclear (MNCs). TRAP+ve MNCs were generated on bone slices from PBMCs treated with ODF (55 ng/ml) and M-CSF (25 ng/ml) for 21 days. a, b, c denote significant difference, p>0.05, ANOVA, Fischer's multiple comparison.
Figure 3:
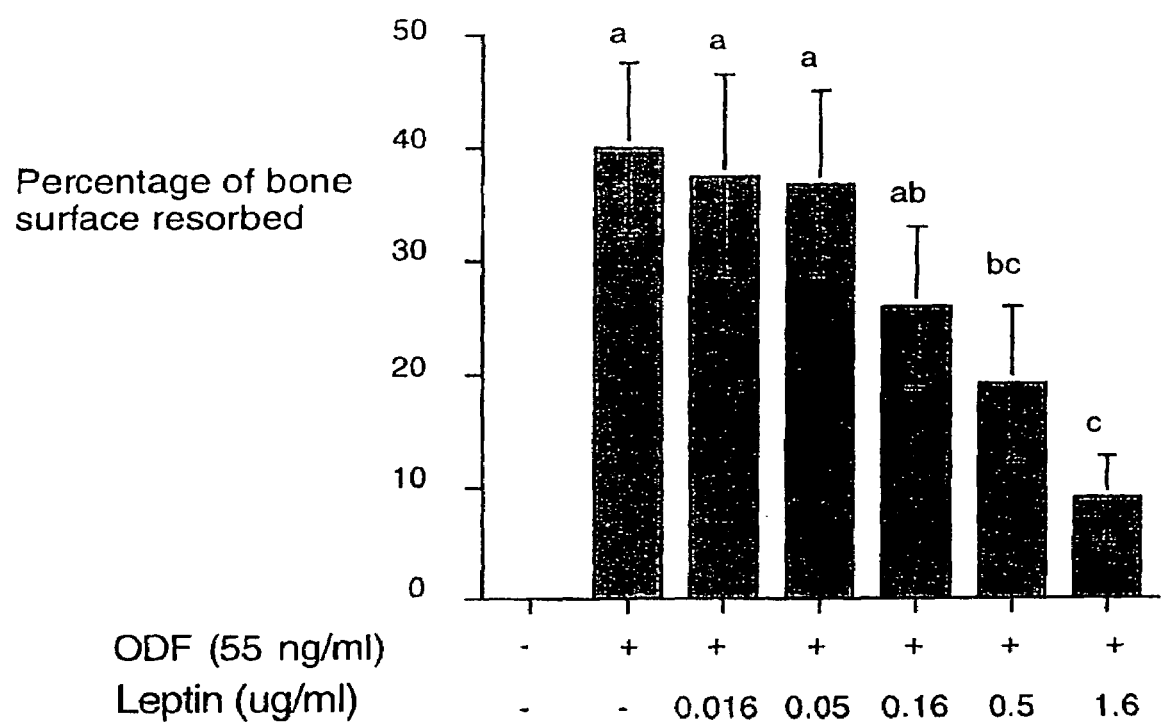
FIG. 3 is a graphical representation showing the effect of leptin on bone resorption by ODF/M-CSF generated human osteoclasts. The percentage of bone surface resorbed by human osteoclast generated from PBMCs was quantified by SEM. a, b, c denotes significant difference, p>0.05, ANOVA, Fischer's multiple comparison.

The inventors found that leptin was a potent inhibitor of ODF-dependent osteoclast (TRAP+ve, CTR+ve MNCs) formation (FIG. 1 and Table 3) and that this effect was dose-dependent (FIG. 2). Consistent with this, was a corresponding dose-dependent decrease in bone resorption (FIG. 3). At the highest concentration used (1.6 µg/ml), leptin reduced the number of osteoclasts and plan area of bone resorption by approximately 80%.

Figure 4A:
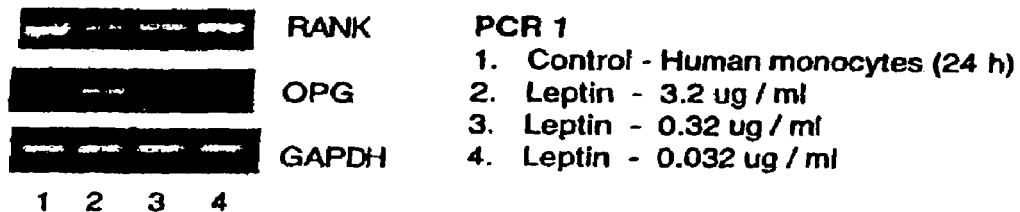
FIG. 4 shows photographic and graphical representations of the effects of leptin on OPG and RANK mRNA expression. Adherent PBMCs were treated with leptin for 24 hr immediately after settlement. The expression of OPG, RANK and GAPDH mRNA in human PBMCs was quantified using semi-quantitative RT-PCR (A). The net intensity of OPG and RANK product bands of mRNA expression were analysed and corrected for GAPDH (B).
Figure 4B:
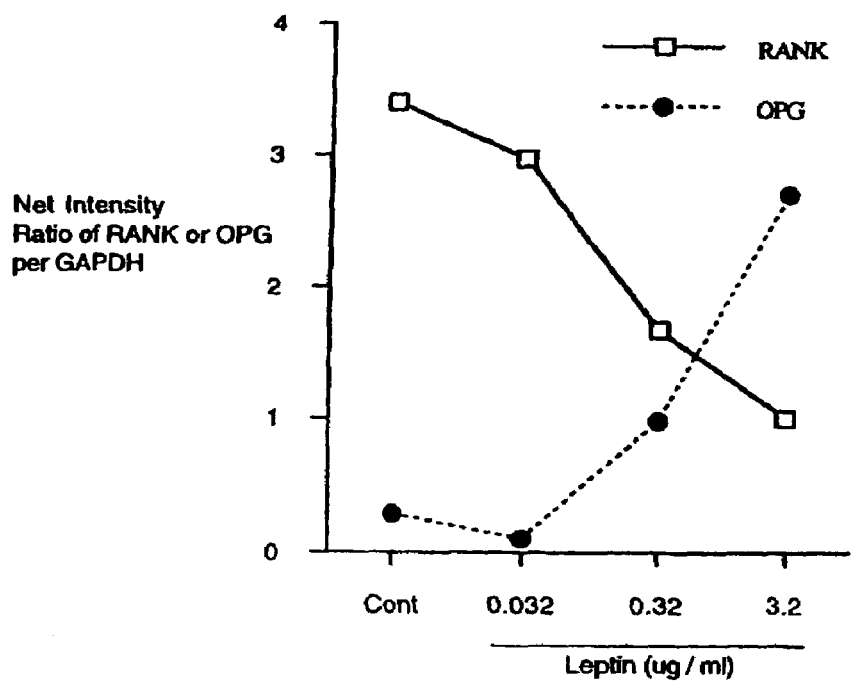

Although not intending to limit the present invention to any one theory or mode of action, the inventors postulated that the mechanism of the antagonistic effect of leptin on ODF-induced osteoclast generation might be related to stimulation of ODF's decoy receptor, OPG and/or inhibition of its target cell receptor, RANK. To test this hypothesis, PBMCs were treated with increasing concentrations of leptin for 24 hrs and OPG and RANK mRNA expression assessed by RT-PCR. It was found that leptin (0.032–3.2 µg/ml) increased OPG mRNA and decreased RANK mRNA in a dose-dependent manner (FIG. 4). The OPG and RANK PCR products were confirmed by restriction enzyme digest. (The OPG response will be confirmed by RNAse protection assay and/or "real-time" PCR).

The inhibitory effect of leptin on osteoclast generation is also seen in co-cultures of osteoblast-like UMR 106-01 cells and PBMCs, which do not require the addition of ODF since it is produced by the UMR 106-01. Treatment of a number of osteoblast (rat calvarial, UMR 106-01, SAOs-2) and stromal (ST2, giant cell tumour, M3T3-L1) cells with leptin had no consistent effect on expression of OPG, ODF or RANK mRNA.

TABLE 3

Effect of leptin on the generation of calcitonin receptor positive (CTR + ve) cells
Adherent PBMC's cultured on bone slices for 3 weeks in MEM/MCSF (25 ng/ml) ± ODF (30 ng/ml) ± Leptin (1.6 µg/ml). Bone slices reacted for TRAP activity and calcitonin binding determined autoradiography.

| Treatment | MNC, CTR + ve | Mono | Mono, CTR + ve |
|---|---|---|---|
| MCSF alone | 0 | 1345 ± 270 | 0 |
| MCSF + ODF | 367 ± 50 | 55 ± 9 | 16 ± 4 |
| MGSF + ODF + Leptin | 0 | 1380 ± 360 | 9 ± 3 |

EXAMPLE 3

Gene Expression by Semi-Quantitative RT-PCR

Cultured cells were directly lysed in RNAzol B solution and total RNA extracted according to the manufacturer's instructions. For RT and PCR reactions, a Perkin Elmer/Cetus DNA Thermal Cycler was used. Reverse transcription was performed in the presence of 5 mM $MgCl_2$, 1 mM deoxynucleotide mix, 3.2 mg random primers, 50 units RNase inhibitor and 20 units AMV reverse transcriptase. The final mixture was reacted at 25° C. for 10 min, 42° C. for 60 min and 95° C. for 5 min to denature the enzyme.

Sense and antisense primers were designed using the MacVector program and synthesised by Gibco BRL, (Gaithersburg, Md.). Sequences and sizes are defined in Table 4.

TABLE 4

| Gene | Forward Primer | Backward Primer | Product Size |
|---|---|---|---|
| GAPDH | 5=CAGTCAGCCGCATCTTCTTTTG 3= (SEQ ID NO:3) | 5=TGGTTCACACCCATGACGAAC 3= (SEQ ID NO:4) | 464 bp |
| OPG | 5=GTACGTCAAGCAGGAGTGCAATC 3= (SEQ ID NO:5) | 5=TTCTTGTGAGCTGTGTTGCCG 3= (SEQ ID NO:6) | 472 bp |
| RANK | 5=TTAAGCCAGTGCTTCACGGG 3= (SEQ ID NO:7) | 5=ACGTAGACCACGATGATGTCGC 3= (SEQ ID NO:8) | 497 bp |

PCR products were confirmed by restriction enzyme digest and all primer pairs spanned intron-exon splice sites allowing for the detection of mRNA only.

PCR amplification was performed with cycles of denaturation at 95° C. for 1 min, annealing at 55° C. for 2 min, and extension at 72° C. for 1 min. The reaction mixture contained 40 pmol of each primer, 200 mM dNTPs, 2 ml of 10× reaction buffer, optimised concentrations of $MgCl_2$; 0.75 mM (OPG), and 1.0 mM (GAPDH and Rank), 1U Taq DNA polymerase, and sterile distilled water up to 20 ml. The mixture was then overlayed with paraffin oil. For semi-quantitative RT-PCR analysis, the optimal number of cyles for each gene was determined as follows: GAPDH, 20 cycles, OPG, 32 cycles and Rank, 30 cycles. PCR products were resolved on a 1.2% w/v agarose gel and visualised using ethidium bromide. The size of the bands were confirmed by a 100 bp DNA ladder (Gibco BRL, Gaithersburg, Md.). Complementary DNA from a sample of human giant cell tumour was used a positive control as we found it to express all the genes studied. Band intensities were measured on the Kodak Digital Science™ 1D Image Analysis Software and expressed as a ratio of GAPDH intensity.

EXAMPLE 4

Osteoclastogenesis Assays Employing Purified CD14+ Cells

Figure 5A:
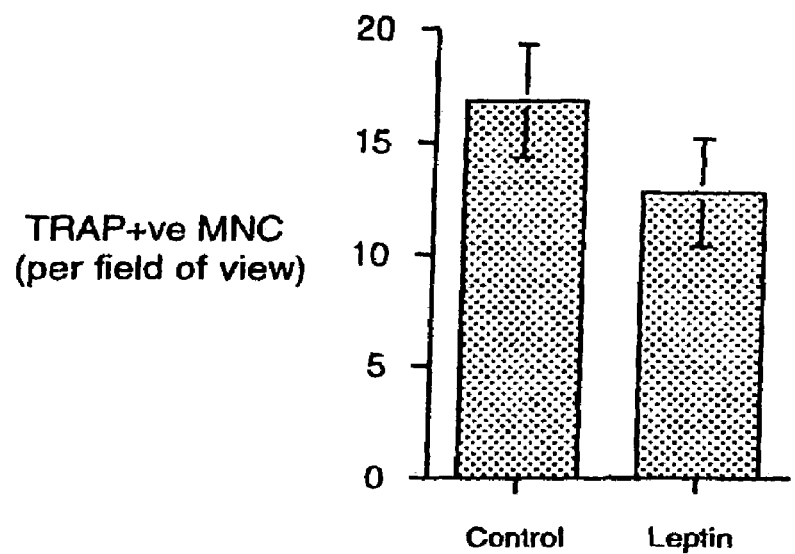
FIG. 5 is a graphical representation of the effect of leptin on osteoclastogenesis in purified CD14+ cells. CD14+ cells were positively selected from unfractionated PBMCs using anti-CD14 antibody labeled immunomagnetic beads and cultured on bone slices for 3 weeks in the presence of M-CSF (25 ng/ml) and ODF (40 ng/ml) with (FIG. 5A) and without (FIG. 5B) leptin 1.5 Fg/ml.
Figure 5B:
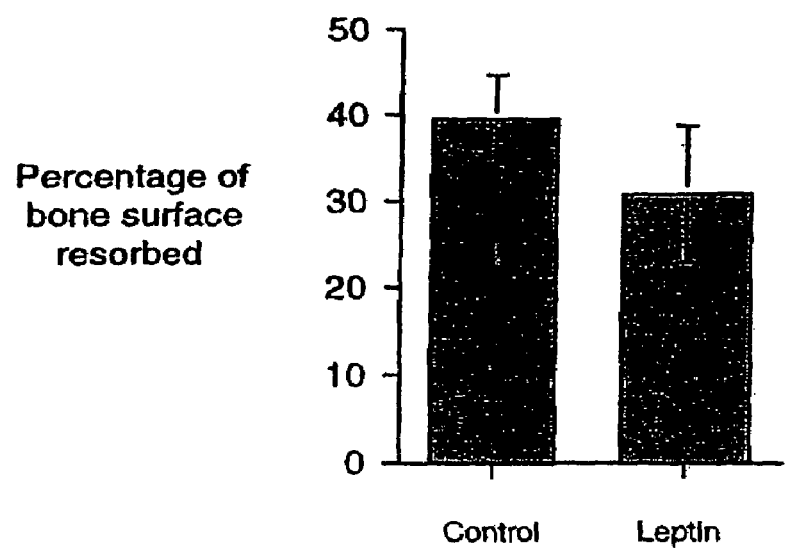

Leptin treatment does not significantly inhibit osteoclastogenesis in assays that use highly purified CD14+ve cells cultured on bone slices for 21 days in the presence of ODF and M-CSF. CD14+ve cells were positively-selected from PBMCs using anti-CD14 antibody-labelled immunomagnetic beads and the VarioMACs system. Purity (90–95%) was confirmed with FACs analysis. CD14+ cells are highly efficient in the production of osteoclasts. PBMC populations depleted of CD14+ve cells (i.e. CD14−ve) are not able to generate osteoclasts in this assay (FIG. 5).

Furthermore, leptin does not upregulate expression of OPG mRNA in purified CD14+ve cells, although down-regulation of RANK mRNA is observed.

These results indicate that the mechanism of leptin-induced inhibition of osteoclastogenesis is not via a direct effect of leptin on CD14+ cells, which appear to be the predominant adherent osteoclast precursor present in the PBMC fraction.

Thus, leptin appears to be acting via another cell type(s) present in the PBMC fraction. At this time the identity of this cell(s) is unknown.

Figure 6:
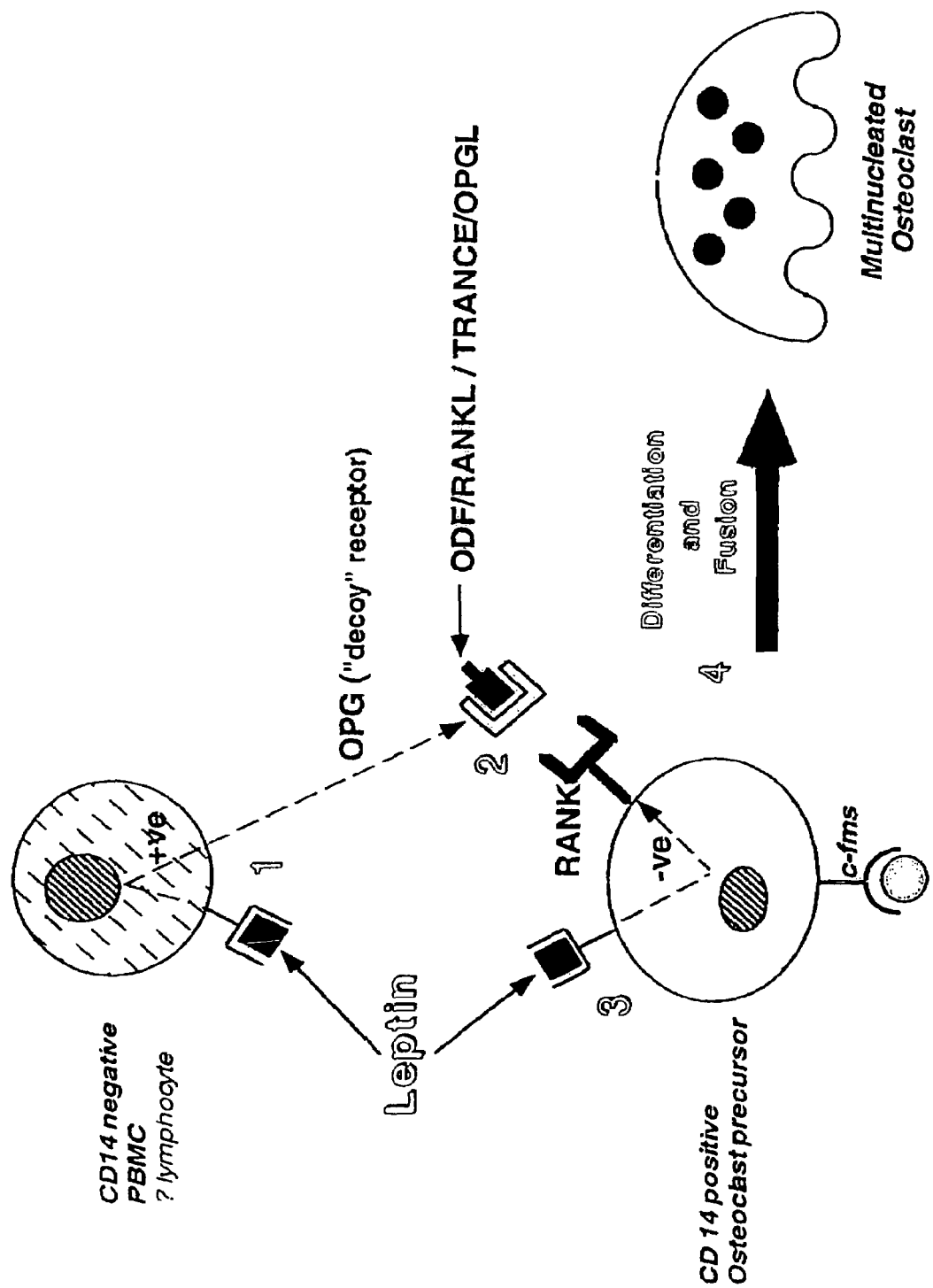
FIG. 6 is a schematic representation of the proposed mechanism of leptin inhibition of osteoclastogenesis. Not shown on the figure is the likely production of leptin by bone marrow adipocytes.

The proposed mechanism of inhibition of osteoclast generation by leptin is shown in FIG. 6.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Auwerx et al., *The LANCET* 351: 737–742, 1998.
Bonner and Laskey, *Eur. J. Biochem.* 46: 83, 1947.
Friedman et al., *Nature* 395: 763–770, 1998.
Marmur and Doty, *J. Mol. Biol.* 5: 109, 1962.
Matsuzaki et al., *Biochem. Biophys. Res. Commun.* 246: 199–204, 1998.
Quinn et al., *Endocrinology* 139: 4424–4427, 1998.
Simonet et al., *Cell* 89: 309–319, 1997.
Suda et al., *Endocrine Reviews* 13: 66–80, 1992.
Suda et al., *Endocrine Reviews* 20: 345–357, 1999.
Yasuda et al., *Endocrinology* 139: 1329–1337, 1998.

What is claimed is:

1. A method of delaying onset of bone resorption in an animal in which bone resorption has not yet occurred, said method comprising:
administering to said animal an effective amount of a leptin or a derivative, homologue, analogue, chemical equivalent or agonist thereof for a time and under conditions sufficient to inhibit, reduce or otherwise delay onset or progression of bone resorption.

2. The method according to claim 1 wherein the leptin or its derivative, homologue or agonist comprises an amino acid sequence having at least 60% similarity to the amino acid sequence set forth in SEQ ID NO:2 after optimal alignment.

3. The method according to claim 1, wherein the leptin or its derivative, homologue or agonist is encoded by the nucleotide sequence set forth in SEQ ID NO:1 or a nucleotide sequence having at least 60% similarity to SEQ ID NO:1 after optimal alignment or a nucleotide sequence capable of hybridizing to SEQ ID NO:1 or its complementary from under low stringency conditions at 42° C.

4. The method according to claim 1 wherein said bone resorption is a result of osteoporosis or Paget's disease.

5. The method of claim 1 wherein said animal is a human.

6. A method of inhibiting, reducing or otherwise delaying onset or progression of symptoms of Paget's disease, said method comprising administering to an animal with Paget's disease an effective amount of leptin or a derivative, homologue, analogue, chemical equivalent or agonist thereof for a time and under conditions sufficient to inhibit, reduce or otherwise delay onset or progression of said symptoms.

7. The method according to claim 6 wherein the leptin or its derivative, homologue or agonist comprises an amino acid sequence having at least 60% similarity to the amino acid sequence set forth in SEQ ID NO:2 after optimal alignment.

8. The method according to claim 6, wherein the leptin or its derivative, homologue or agonist is encoded by the nucleotide sequence set forth in SEQ ID NO: 1 or a nucleotide sequence having at least 60% similarity to SEQ ID NO: 1 after optimal alignment or a nucleotide sequence capable of hybridizing to SEQ ID NO:1 or its complementary from under low stringency conditions at 42° C.

9. The method of claim 6 wherein said animal is a human.

* * * * *

SEQUENCE LISTING

<160> NUMBER OF SEQ ID NOS: 8

<210> SEQ ID NO 1
<211> LENGTH: 504
<212> TYPE: DNA
<213> ORGANISM: Homo sapiens
<220> FEATURE:
<221> NAME/KEY: CDS
<222> LOCATION: (1)...(504)

<400> SEQUENCE: 1

| atg | cat | tgg | gga | acc | ctg | tgc | gga | ttc | ttg | tgg | ctt | tgg | ccc | tat | ctt | 48 |
| Met | His | Trp | Gly | Thr | Leu | Cys | Gly | Phe | Leu | Trp | Leu | Trp | Pro | Tyr | Leu | |
| 1 | | | | 5 | | | | | 10 | | | | | 15 | | |

| ttc | tat | gtc | caa | gct | gtg | ccc | atc | caa | aaa | gtc | caa | gat | gac | acc | aaa | 96 |
| Phe | Tyr | Val | Gln | Ala | Val | Pro | Ile | Gln | Lys | Val | Gln | Asp | Asp | Thr | Lys | |
| | | | 20 | | | | | 25 | | | | | 30 | | | |

| acc | ctc | atc | aag | aca | att | gtc | acc | agg | atc | aat | gac | att | tca | cac | acg | 144 |
| Thr | Leu | Ile | Lys | Thr | Ile | Val | Thr | Arg | Ile | Asn | Asp | Ile | Ser | His | Thr | |
| | | | 35 | | | | | 40 | | | | | 45 | | | |

| cag | tca | gtc | tcc | tcc | aaa | cag | aaa | gtc | acc | ggt | ttg | gac | ttc | att | cct | 192 |
| Gln | Ser | Val | Ser | Ser | Lys | Gln | Lys | Val | Thr | Gly | Leu | Asp | Phe | Ile | Pro | |
| | 50 | | | | | 55 | | | | | 60 | | | | | |

| ggg | ctc | cac | ccc | atc | ctg | acc | tta | tcc | aag | atg | gac | cag | aca | ctg | gca | 240 |
| Gly | Leu | His | Pro | Ile | Leu | Thr | Leu | Ser | Lys | Met | Asp | Gln | Thr | Leu | Ala | |
| 65 | | | | | 70 | | | | | 75 | | | | | 80 | |

| gtc | tac | caa | cag | atc | ctc | acc | agt | atg | cct | tcc | aga | aac | gtg | atc | caa | 288 |
| Val | Tyr | Gln | Gln | Ile | Leu | Thr | Ser | Met | Pro | Ser | Arg | Asn | Val | Ile | Gln | |
| | | | | 85 | | | | | 90 | | | | | 95 | | |

| ata | tcc | aac | gac | ctg | gag | aac | ctc | cgg | gat | ctt | ctt | cac | gtg | ctg | gcc | 336 |
| Ile | Ser | Asn | Asp | Leu | Glu | Asn | Leu | Arg | Asp | Leu | Leu | His | Val | Leu | Ala | |
| | | | 100 | | | | | 105 | | | | | 110 | | | |

| ttc | tct | aag | agc | tgc | cac | ttg | ccc | tgg | gcc | agt | ggc | ctg | gag | acc | ttg | 384 |
| Phe | Ser | Lys | Ser | Cys | His | Leu | Pro | Trp | Ala | Ser | Gly | Leu | Glu | Thr | Leu | |
| | | 115 | | | | | 120 | | | | | 125 | | | | |

| gac | agc | ctg | ggg | ggt | gtc | ctg | gaa | gct | tca | ggc | tac | tcc | aca | gag | gtg | 432 |
| Asp | Ser | Leu | Gly | Gly | Val | Leu | Glu | Ala | Ser | Gly | Tyr | Ser | Thr | Glu | Val | |
| | 130 | | | | | 135 | | | | | 140 | | | | | |

| gtg | gcc | ctg | agc | agg | ctg | cag | ggg | tct | ctg | cag | gac | atg | ctg | tgg | cag | 480 |
| Val | Ala | Leu | Ser | Arg | Leu | Gln | Gly | Ser | Leu | Gln | Asp | Met | Leu | Trp | Gln | |
| 145 | | | | 150 | | | | | 155 | | | | | 160 | | |

| ctg | gac | ctc | agc | cct | ggg | tgc | tga | | | | | | | | | 504 |
| Leu | Asp | Leu | Ser | Pro | Gly | Cys | * | | | | | | | | | |
| | | | | 165 | | | | | | | | | | | | |

<210> SEQ ID NO 2
<211> LENGTH: 167
<212> TYPE: PRT
<213> ORGANISM: Homo sapiens

<400> SEQUENCE: 2

| Met | His | Trp | Gly | Thr | Leu | Cys | Gly | Phe | Leu | Trp | Leu | Trp | Pro | Tyr | Leu |
| 1 | | | | 5 | | | | | 10 | | | | | 15 | |

| Phe | Tyr | Val | Gln | Ala | Val | Pro | Ile | Gln | Lys | Val | Gln | Asp | Asp | Thr | Lys |
| | | | 20 | | | | | 25 | | | | | 30 | | |

| Thr | Leu | Ile | Lys | Thr | Ile | Val | Thr | Arg | Ile | Asn | Asp | Ile | Ser | His | Thr |
| | | | 35 | | | | | 40 | | | | | 45 | | |

| Gln | Ser | Val | Ser | Ser | Lys | Gln | Lys | Val | Thr | Gly | Leu | Asp | Phe | Ile | Pro |
| | 50 | | | | | 55 | | | | | 60 | | | | |

```
Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 3
<211> LENGTH: 22
<212> TYPE: DNA
<213> ORGANISM: Artificial Sequence
<220> FEATURE:
<223> OTHER INFORMATION: GAPDH forward primer.

<400> SEQUENCE: 3
cagtcagccg catcttcttt tg                                            22

<210> SEQ ID NO 4
<211> LENGTH: 21
<212> TYPE: DNA
<213> ORGANISM: Artificial Sequence
<220> FEATURE:
<223> OTHER INFORMATION: GAPDH backward primer.

<400> SEQUENCE: 4
tggttcacac ccatgacgaa c                                             21

<210> SEQ ID NO 5
<211> LENGTH: 23
<212> TYPE: DNA
<213> ORGANISM: Artificial Sequence
<220> FEATURE:
<223> OTHER INFORMATION: OPG forward primer.

<400> SEQUENCE: 5
gtacgtcaag caggagtgca atc                                           23

<210> SEQ ID NO 6
<211> LENGTH: 21
<212> TYPE: DNA
<213> ORGANISM: Artificial Sequence
<220> FEATURE:
<223> OTHER INFORMATION: OPG backward primer.

<400> SEQUENCE: 6
ttcttgtgag ctgtgttgcc g                                             21

<210> SEQ ID NO 7
<211> LENGTH: 20
<212> TYPE: DNA
<213> ORGANISM: Artificial Sequence
<220> FEATURE:
<223> OTHER INFORMATION: RANK forward primer.

<400> SEQUENCE: 7

```
ttaagccagt gcttcacggg                                           20

<210> SEQ ID NO 8
<211> LENGTH: 22
<212> TYPE: DNA
<213> ORGANISM: Artificial Sequence
<220> FEATURE:
<223> OTHER INFORMATION: RANK backward primer.

<400> SEQUENCE: 8
acgtagacca cgatgatgtc gc                                        22
```